(12) United States Patent
Holmström et al.

(10) Patent No.: US 6,985,772 B2
(45) Date of Patent: Jan. 10, 2006

(54) CARDIAC PACEMAKER WITH AUTOMATIC ADAPTATION OF PACING RATE TO CARDIAC OUTPUT

(75) Inventors: Nils Holmström, Järfälla (SE); Kjell Norén, Solna (SE)

(73) Assignee: St. Jude Medical AB, Jarfalla (SE)

( * ) Notice: Subject to any disclaimer, the term of this patent is extended or adjusted under 35 U.S.C. 154(b) by 447 days.

(21) Appl. No.: 10/267,239

(22) Filed: Oct. 9, 2002

(65) Prior Publication Data

US 2003/0078628 A1    Apr. 24, 2003

(30) Foreign Application Priority Data

Oct. 22, 2001   (SE)   .................... 0103513

(51) Int. Cl.
*A61N 1/368*   (2006.01)
(52) U.S. Cl. .................. 607/9; 607/4; 607/18
(58) Field of Classification Search ............ 607/9, 607/14–15, 17–18, 23–24
See application file for complete search history.

(56) References Cited

U.S. PATENT DOCUMENTS

| | | | |
|---|---|---|---|
| 4,928,688 A | 5/1990 | Mower ............................ | 607/9 |
| 5,183,040 A | 2/1993 | Nappholz et al. .............. | 607/4 |
| 5,540,727 A | 7/1996 | Tockman et al. .............. | 607/18 |
| 5,800,465 A * | 9/1998 | Thompson et al. ............. | 607/9 |
| 5,873,895 A | 2/1999 | Sholder et al. ................. | 607/9 |
| 6,473,645 B1 * | 10/2002 | Levine ........................... | 607/9 |
| 6,748,261 B1 * | 6/2004 | Kroll et al. ................. | 600/510 |
| 2001/0005790 A1 | 6/2001 | Ripart | |
| 2003/0074029 A1 * | 4/2003 | Deno et al. ................... | 607/23 |

FOREIGN PATENT DOCUMENTS

| WO | WO 98/14772 | 4/1998 |
|---|---|---|
| WO | WO 01/80947 | 11/2001 |

* cited by examiner

*Primary Examiner*—Carl Layno
(74) *Attorney, Agent, or Firm*—Schiff Hardin LLP

(57) ABSTRACT

A pacemaker has a pulse generator for delivering stimulation pulses to a patient's heart, a sensor for measuring a parameter related to cardiac output, and a control unit for controlling the delivery of stimulation pulses from the pulse generator. The control unit includes an altering unit for altering at least one of the VV delay between consecutive stimulation pulses to the right and left ventricles and the AA delay between consecutive stimulation pulses to the right and left atria. The sensor measures the parameter in various time windows within a time of operation of predetermined VV- or AA-delay values. A determining unit includes a calculation unit for calculating an average value of the measured parameter during each of said time windows and the determining unit uses these average values to determine which one of the VV- and/or AA-delay values results in a higher cardiac output.

19 Claims, 4 Drawing Sheets

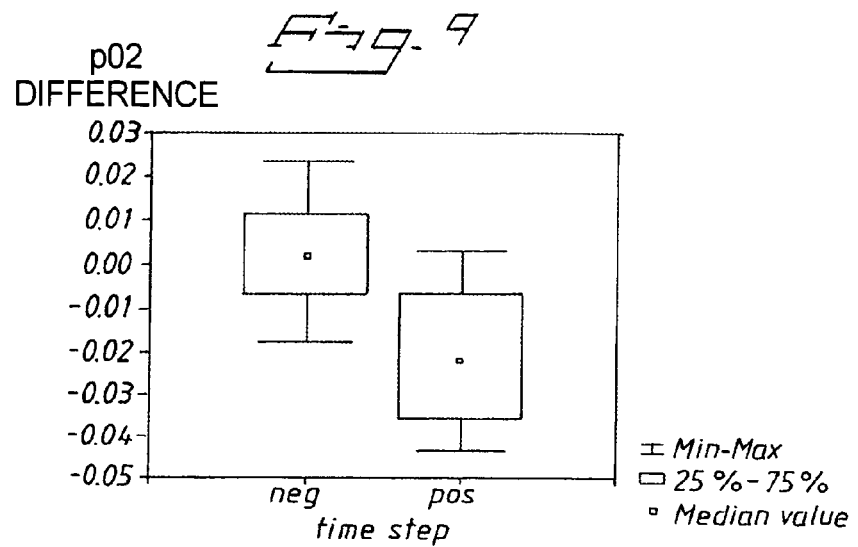
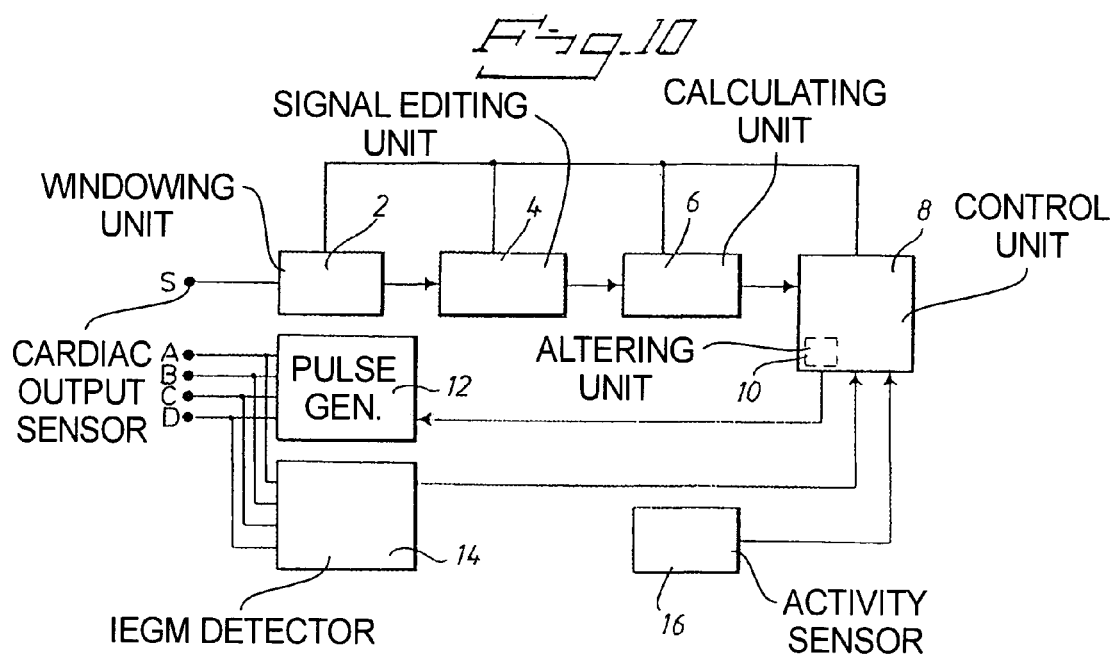

CARDIAC PACEMAKER WITH AUTOMATIC ADAPTATION OF PACING RATE TO CARDIAC OUTPUT

BACKGROUND OF THE INVENTION

1. Field of the Invention

The present invention relates to a pacemaker having a pulse generator for delivering stimulation pulses to a patient's heart, a control unit for controlling the delivery of stimulation pulses from the pulse generator, and a sensor provided to measure a parameter related to cardiac output of the patient.

2. Description of the Prior Art

In multi-site stimulation the PV-interval between the occurrence of an intrinsic P-wave and the application of a cardiac stimulation pulse in the ventricle can be different from the AV-interval between consecutive cardiac stimulation pulses to the atrium and the ventricle, and the PA-interval between the occurrence of an intrinsic P-wave in the right atrium and the application of a cardiac stimulation pulse in the left atrium can be different from the AA-interval between consecutive cardiac stimulation pulses to the right and left atria. The term AV-delay means in the interval between the occurrence of a paced or an intrinsic P-wave and the application of a cardiac stimulation pulse to the ventricle of the heart, and AA-delay means the interval between the occurrence of a paced or an intrinsic P-wave in the right atrium and the application of a cardiac stimulation pulse to the left atrium of the heart.

In cardiac therapy there is a primary aim to stimulate the heart such that the natural manner of a heart's functioning is re-established as far as possible. The heart is then working with a minimum waste of energy.

It is well known that cardiac output of a human being is depending on the AV-delay, see e.g. Swedish patent application no. 001534-7, corresponding to published PCT Application WO 01/80947.

In this application experimental data obtained from an animal study illustrate the dependence of several cardiac performance parameters on the AV-delay (or PV-delay). A changed AV-delay has an instant effect on the stroke volume SV but can also be observed on the mixed or central venous pressure $P_vO_2$ after a circulatory delay. A maximum $P_vO_2$ response was in the animal studies observed 50–80 s after the AV change. Thereafter it declined due to autonomic compensation. Thus, $P_vO_2$ mirrors the left heart's performance and reflects the cardiac output and its transient response can be used to optimize the AV-delay according to the algorithm described therein. Simultaneously the parameters oxygen saturation $SO_2$ and carbon dioxide $CO_2$ can be used for this purpose. The carbon dioxide concentration $CO_2$ will, however, decrease in the same degree as the oxygen concentration increases.

It is also known from e.g. U.S. Pat. No. 4,928,688 to pace both ventricles of a heart to produce simultaneous contraction of both ventricles, thereby assuring hemodynamic efficiency. In this U.S. patent only simultaneous pacing of both ventricles is proposed. In U.S. Pat. No. 5,540,727 optimization of the pacing by selective stimulation in both atria and both ventricles with certain interatrial AA-, VV-, and AV-delays is described.

SUMMARY OF THE INVENTION

An object of the present invention is to improve the possibilities of determining the dependence of different cardiac performance parameters on at least one of the time-delays VV-delay and AA-delay, such that significant information can be extracted as well from such parameters as the oxygen pressure (pO2) and oxygen saturation (SO2).

The above object is achieved in accordance with principles of the present invention in a pacemaker having a pulse generator for delivering stimulation pulses to a patient's heart and a control unit for controlling the delivery of stimulation pulses from the pulse generating means. A sensor is provided to measure a parameter related to cardiac output of the patient. The control unit includes an altering unit for altering at least one of the VV-delay between consecutive stimulation pulses to the right and left ventricles and the AA-delay between consecutive stimulation pulses to the right and left atria, from a predetermined first VV- or AA-delay value to a predetermined second VV- or AA-delay value, and back to the first VV- or AA-delay value. The sensor measures the parameter in a time window within a time of operation with the predetermined first VV- or AA-delay value, in a time window within a time of operation with the predetermined second VV- or AA-delay value and in a time window within a time of operation after the return back to the first VV- or AA-delay value. A determining unit includes a calculation unit for calculating an average value of the measured parameter during each of said time windows and the determining unit uses these average values to determine which one of the VV- and/or AA-delay values results in a higher cardiac output.

Thus, by using a technique analogous to that described in the above-mentioned Swedish Patent Application No. 001534-7 significant information can also be extracted from such parameters as oxygen pressure pO2 or oxygen saturation SO2 for determining the dependency of cardiac output on the VV-delay and/or the AA-delay. This is an important advantage since especially the pO2 sensor has appeared to be especially suitable to use for this type of measurement. The technique according to the invention of course also can be applied on other measured cardiac performance parameters in order to obtain more distinct results, in particular if the measurement signals are affected by disturbances in one way or the other.

In an embodiment of the pacemaker according to the invention the calculation unit forms a first difference between average values obtained during the window positioned within the time of operation with the first VV- or AA-delay value and obtained during the time window positioned within the time of operation with the second VV- or AA-delay value. The calculation unit forms a second difference between average values obtained during the time window positioned within the time of operation with the second VV- or AA-delay value and the time window positioned within the time of operation after the return of the VV- or AA-delay back to the first VV- or AA-delay value. The calculation unit uses the first and second differences to determine which VV- or AA-delay results in a higher cardiac output. In this way the possibility of extracting reliable information from the measurement signals is even further improved.

In another embodiment of the pacemaker according to the invention, the altering unit repeatedly alters the VV- or AA-delay a number of times between the predetermined first and second VV- or AA-delay values, and the calculation unit forms an average value of a resulting number of the first differences and an average value of a number of the second differences. The calculation unit uses the average values to determine which VV-and/or AA-delay values result in a higher cardiac output. The possibility of extracting information from the measurement signals is then further improved.

In a further embodiment of the pacemaker according to the invention the altering unit, after determination of which of the first and second VV- or AA-delay values indicates a higher cardiac output, alters the VV- or AA-delay between this better value of the first and second VV- or AA-delay values, and a third VV- or AA-delay value. The determining unit then determines which of the better VV- or AA-delay value and the third AV-delay value results in an indication of a higher cardiac output. The altering unit repeats this procedure until VV- and/or AA-delay values are determined which result in an indication of a highest cardiac output. Thus the pacemaker according to the invention will automatically find the optimum VV- and/or AA-delay values and will then toggle around these optimum values. If conditions should change such that other VV- and/or AA-delay values are needed to obtain a maximum cardiac output, the pacemaker will automatically find this new optimum delay values.

In another embodiment of the pacemaker according to the invention the altering unit alters the A-V delay, in addition to at least one of the VV-delay and AA-delay. The determining unit determines, from the detected changes in the parameter related to cardiac output when altering the VV- and/or AA-delays and the AV-delay, which combination of VV- and/or AA-delay values and AV-delay values results in an indication of highest cardiac output. Thus the VV-delay or the AA-delay together with the AV-delay can be adjusted to give an optimum cardiac output, or all three time-delays VV-, AA- and AV-delays can be adjusted to give an optimum cardiac output.

In another embodiment of the pacemaker according to the invention the altering unit alters the time-delay values after times of operation according to a pseudo-stochastic sequence. Since several biological variations and external disturbances have a cyclic character, which can interfere with the measurements, it is an advantage not to use a cyclic variation of the time-delays but instead to use pseudo-stochastic sequences of delay values. For patients having Left Bundle Branch Block LBBB only the VV-delay is optimized by a pseudo-sequence. For patients with both AV-block and LBBB it is possible to both optimize the AV-delay and the VV-delay by successive iterations.

In another embodiment of the pacemaker according to the invention the time windows are positioned immediately before and immediately after an alteration of the respective time-delay values. In this way changes in the measured parameter related only to the change of the time-delay in question are determined and errors originating from variations in oxygen consumption's of the patient and sensor drift are minimized.

In other embodiments of the pacemaker according to the invention the sensor measuring a parameter related to cardiac output is any of a pO2-sensor, a SO2-sensor, an average blood pressure sensor, a coronary artery flow sensor or a sinus rate sensor, and said blood pressure sensor preferably measures the blood pressure in the vena cava or the right atrium. Arterial blood pressure, average blood pressure, systolic and diastolic pressure all correlate to cardiac output.

DESCRIPTION OF THE DRAWINGS

FIG. 9 is a diagram illustrating the spread and medium value of pO2 differences obtained from the data shown in FIG. 3.

FIG. 10 is a block diagram of a closed loop regulation system of the pacemaker according to the invention.

DESCRIPTION OF THE PREFERRED EMBODIMENTS

Figure 1:
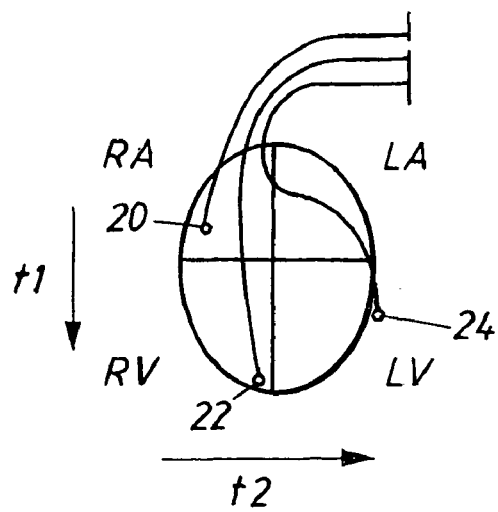
FIGS. 1 and 2 illustrates generally a 3-chamber and a 4-chamber heart stimulator respectively.
Figure 2:
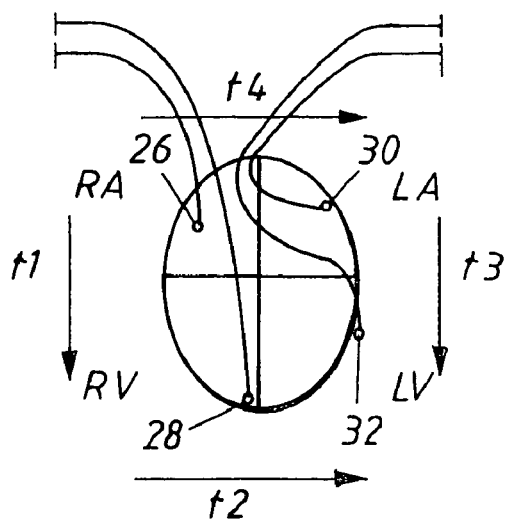

FIGS. 1 and 2 illustrate two examples of multi-site stimulation.

In the 3-chamber stimulation system shown in FIG. 1 electrodes 20, 22, 24 are positioned in the right atrium RA, the right ventricle RV and the left ventricle LV respectively. LA denotes the left atrium.

In the 4-chamber system shown in FIG. 2 electrodes 26, 28, 30 and 32 are positioned in the right atrium RA, the right ventricle RV, the left atrium LA and the left ventricle LV respectively.

In FIG. 1 biventricular 3-chamber stimulation is thus illustrated and in FIG. 2 biatrial and biventricular 4-chamber stimulation is shown. In the 3-chamber stimulation according to FIG. 1 two time delays are of interest, viz. the ordinary AV-delay designated t1 and the VV-time delay designated t2. In the 4-chamber system shown in FIG. 2 three time delays are of interest, viz. the ordinary AV-delay t1, the VV-delay t2, and the AA-delay t4.

The AV-delay t1 on the right side of the heart can be different from the AV-delay t3 on the left side of the heart. It should also be noted that $t1 \approx t2+t3$ (see W Koglek).

With the technique described below each of the above mentioned time-delays or time intervals can be optimized, and by successive iterations the optimal timing can be obtained by the method described in the following.

It should also be noted that the time settings t1–t4 above are different for sensed and stimulated invents as pointed out above and therefore should be optimized separately.

Figure 3:
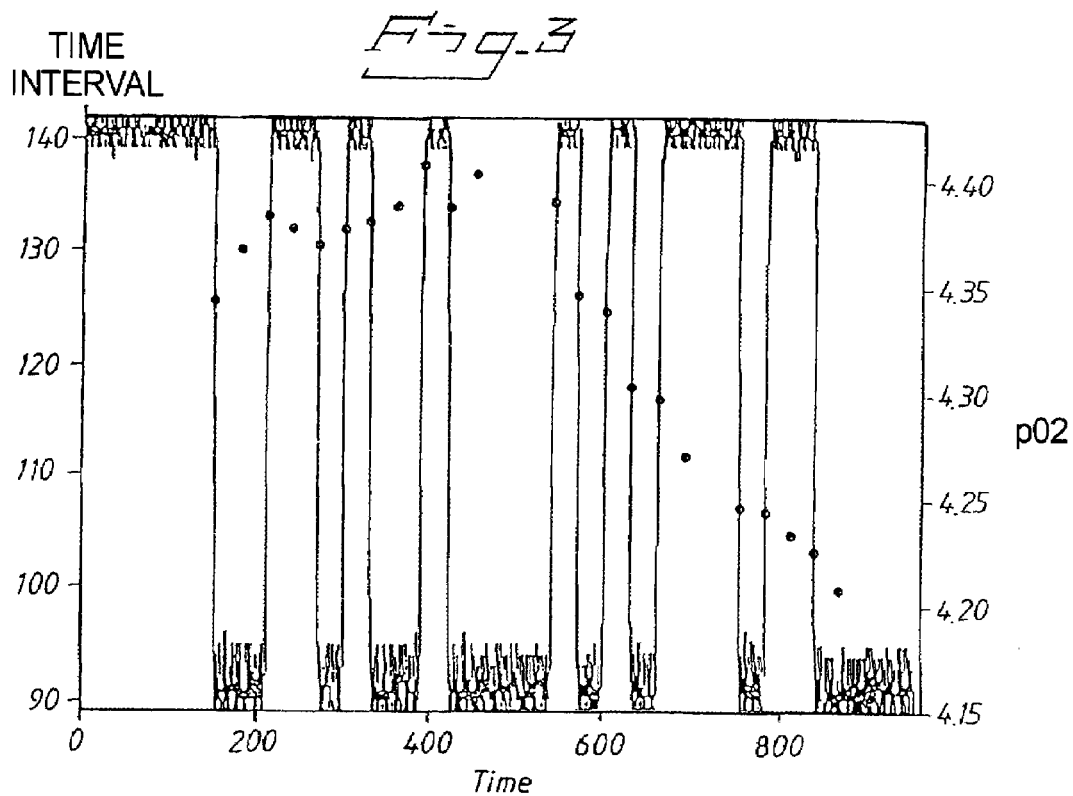
FIG. 3 shows qualitatively the time delay and the average pO2 as a function of time.

FIG. 3 shows qualitatively the time interval VV- or AA-delay as a function of time. In this diagram dots are shown representing the average value of the measured pO2 during a predetermined period of time immediately before and immediately after each change in the time-delay. The marked values are average values during a predetermined time immediately preceding the position of the dot.

Figure 4:
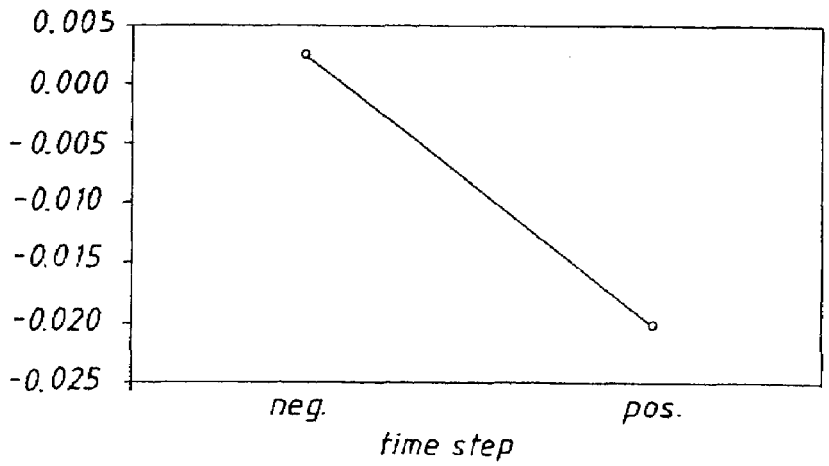
FIG. 4 illustrates the result obtained by analysis of the data in FIG. 3 by the pacemaker according to the invention.

FIG. 4 shows the average value of the difference pO2-diff between each pair of average values from opposite sides of transitions between two time delay values for negative transitions, to the left in FIG. 4, and for positive transitions, to the right in the FIG. 4. From FIG. 4 it can be seen that a negative time transition increases the pO2-difference whereas a positive time step decreases the pO2-difference. This significant difference between the two pO2-differences indicates that the shorter time delay is more effective than the longer delay in this example.

In FIG. 9 the minimum and maximum values of the used pO2 differences are shown as well as the 25%–75% spread of these values and the median values.

Corresponding diagrams can be obtained for the SO2 difference, the central venous pressure difference, the average blood pressure difference, the carotid artery flow difference and the sinus rate difference.

As mentioned above it is possible to identify hemodynamic improvements of cardiac output by measuring changes in O2 after a step change of a time-delay. The oxygen contents can be measured electrochemically, by a pO2-sensor, or optically by a SO2 sensor.

Thus in the example described above the time delay, or the timing of the pulse generator of the pacemaker, is altered between two settings, e.g. a level A and a level B, one of which is the "better" one. By forming the difference between the average oxygen content, $\Delta p$ (AB) during a time window of predetermined length immediately before a change of the time delay and during a time window of the same length immediately after the change from level A to level B, and comparing this result with the corresponding difference, $\Delta p$ (BA), when the AV-delay is changed in the opposite direction from level B to level A, it is possible to find the best setting, A or B. The described procedure can be repeated and the results averaged for obtain a better resolution as described above.

If $\Delta p(AB) < \Delta p(BA)$ setting A for the time delay gives a higher O2 content indicating a better ventricular performance.

If, on the other hand, $\Delta p(AB) > \Delta p(BA)$ setting B for the time delay give a better cardiac performance.

Figure 5:
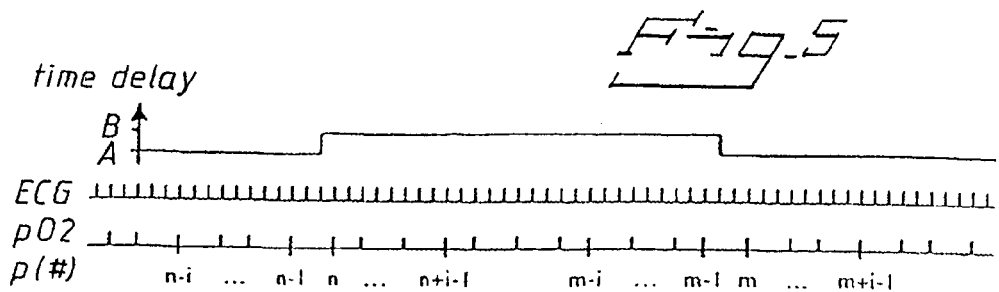
FIG. 5 illustrates the differential technique implemented in the pacemaker according to the invention to obtain an optimum AV-delay.

In FIG. 5 p(#) designates oxygen measurements and n designates a first oxygen measurement p(n) after a step change of the time delay from level A to level B, and m designates first oxygen measurement p(m) after a change of time delay from level B to level A. The number of averaged O2 samples is denoted by i. In FIG. 5, i=4.

FIG. 5 illustrates the differential technique according to the invention for selecting the best time delay value as explained above.

After n+i−1 measurements of O2 it is possible to calculate the O2 response of a change of the time delay from level A to level B according to the equation.

$$\Delta p(AB) = \frac{1}{i}\left(\sum_{x=1}^{i} p(n-x) - \sum_{x=1}^{i} p(n+x-1)\right)$$

After m+i−1 O2 measurements it is possible to calculate the O2 response of a change of the time delay from level B to level A according to equation $$\Delta p(BA) = \frac{1}{i}\left(\sum_{x=1}^{i} p(m-x) - \sum_{x=1}^{i} p(m+x-1)\right)$$

By repeating this procedure several times the risk of fault decisions is practically eliminated. The corresponding mean values $\psi$ (A, B) are given by the following equations $$\Psi(AB) = \frac{1}{u}\sum_{x=1}^{u} \Delta p(AB)(x)$$

$$\Psi(BA) = \frac{1}{u}\sum_{x=1}^{u} \Delta p(BA)(x)$$

wherein u designates the number of times the procedure was repeated.

Thus if $\Psi(AB) < \Psi(BA)$ the time delay value B does not improve the heart performance compared to the situation with a time-delay value equal to level A.

Figure 6:
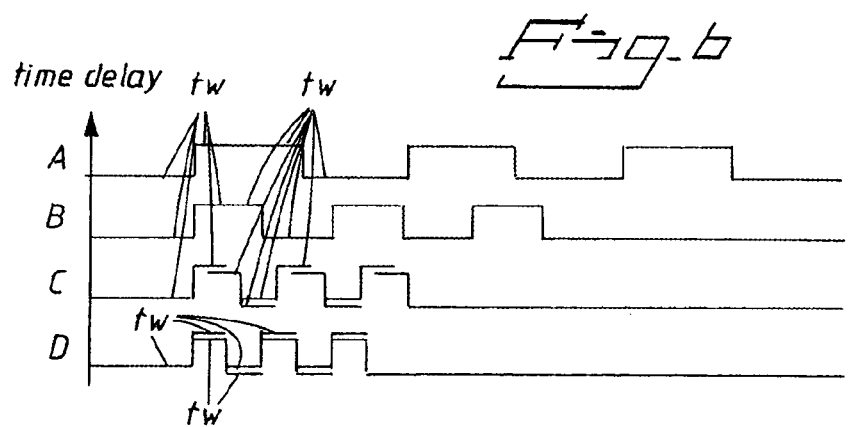
FIG. 6 illustrates different types of sampling measured parameter values.

Different types of differentiation of the O2 signal can be used. In the example above and in situations "A" and "B" in FIG. 6 the time windows, in which the measurements are performed, i.e. the measurements samples are taken, do not overlap. In the type of differentiation illustrated at "C" and "D" in FIG. 6 the same measurement samples are sometimes used twice, since adjacent time windows, in which the measurements are carried out, overlap. The time windows in question are designated tw. Curve A illustrates a situation with an intermediate time interval between each couple of time windows in which measurements are performed, curve B illustrates a situation in which consecutive measurement time windows directly follow each other, curve C illustrates a situation with partially overlapping measurement time windows and curve D illustrates a situation in which the time windows are totally overlapping.

Figure 7:
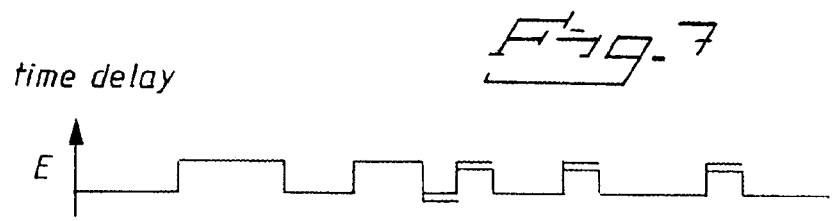
FIG. 7 shows a pseudo-stochastic AV-delay sequence.

It is an advantage not to use a cyclic variation of the time delays, since many biological variations and external disturbances are cyclic which consequently can interfere with the measurements. Therefore it may be an advantage to change the time delays according to a pseudo-stochastic sequence as illustrated in FIG. 7.

Figure 8:
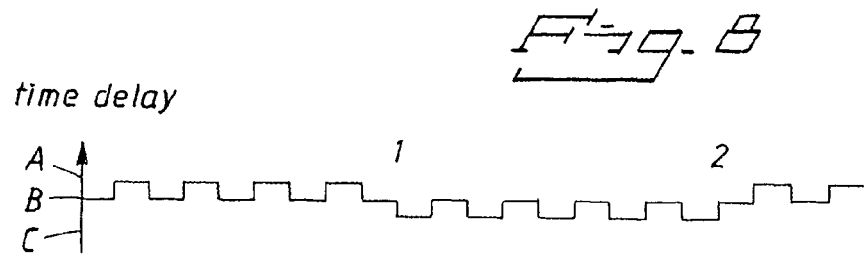
FIG. 8 shows the AV-delay sequence when an optimum time-delay is reached.

When a time delay value has been selected as the "better" one, this "better" value is used in a new comparison procedure in which it is compared with another time delay. In each step of this selection procedure the time delay value is favored which results in the highest O2 value, and when the optimum time delay value is reached, the time delays will toggle around this optimum value, as illustrated in FIG. 8. In the shown example a time delay equal to B is supposed to give a better O2 value than a time delay equal to A. Further, a time delay equal to B is also supposed to give a better O2 value than a time delay equal to C.

Thus, if the situation of the patient changes such that the optimum time delays are changed, the pacemaker according to the invention will automatically find new optimum values and the pacemaker will operate with these new delays.

The differential technique described above is a simple way of eliminating errors originating from variations in oxygen consumption of the patient and sensor drift. It is also advantages to use this technique because the variations of the oxygen content due to time-delay changes are much smaller that changes in the oxygen content due to metabolic variations and other factors.

FIG. 10 shows a block diagram of the basic components of the pacemaker according to the invention. The pacemaker has a sensor S, preferably a pO2-sensor, for measuring a parameter related to cardiac output of the patient (e.g., oxygen pressure). Signals representing this parameter are received from the sensor S via a windowing unit 2, controlled by the control unit 10, within the aforementioned time windows. The measurement signals are processed in a suitable signal processing unit 4 and the average value during predetermined time windows immediately before and after a change in a time delay is calculated in a calculating unit 6. In this calculating unit 6 the difference between average values obtained in the respective time windows on each side of the time delay transition are calculated, and finally an average mean value is determined for this difference for "negative" transitions and "positive" transitions in the time delay, respectively, as described above, for determining which one of the time delay values results in a higher cardiac output. This result is supplied to a control unit 8 including an altering unit 10.

The timing of the pulse generator 12 is then controlled by the altering unit 10 to change the time delay in question between this "better" time delay value and a new time-delay value.

The length of the time window in which the measurements are performed as well as the sampling frequency can be varied by the control unit 8.

An IEGM detector 14 is also connected to the control unit 8, allowing the measurements to be synchronized to the cardiac cycle of the patient.

The optimum time delay at rest is normally longer than at exercise. Different activity levels therefore have to be distinguished. Considerable variations in activity level, however, can give rise to problems. The easiest way to avoid such problems is to inhibit the time delay selection function of the pacemaker when an activity sensor indicates activity of the patient exceeding a predetermined threshold level. An activity sensor 16 is therefore connected to the control unit 8. This activity sensor can be the O2 sensor used and/or e.g. a movement sensor. If an increased activity persists over a longer time it is possible with the pacemaker according to the invention to search for a new optimum time delay(s) at this defined level of workload. In such a state it is advantageous to have a shorter decision time for deciding the optimum time delay(s) than for the "at rest" condition.

The sensor used in the pacemaker according to the invention is preferably an electrochemically pO2-sensor of the type described in PCT Application WO 98/14772. The invention is, however, not limited to the use of such a sensor. A pO2-sensor can be implanted together with an implanted pacemaker, e.g. for measuring the oxygen concentration in the right atrium. However, variations of the oxygen content in e.g. the ventricle or arteria pulmonaris can be continuously measured in a corresponding way. Further, with a pO2-sensor the measuring pulses can be made so short that synchronization of the measurement to the cardiac cycle is possible, and the pO2-sensor has proved to give reliable measurement results over time.

Although modifications and changes may be suggested by those skilled in the art, it is the intention of the inventors to embody within the patent warranted hereon all changes and modifications as reasonably and properly come within the scope of their contribution to the art.

We claim as our invention:

1. A cardiac pacemaker comprising:
    a pulse generator which emits stimulation pulses;
    an electrode system connected to said pulse generator and adapted to deliver respective stimulation pulses to both atria and both ventricles of a heart of a subject, said pulse generator emitting said stimulation pulses with time delays including a VV-delay between consecutive stimulation pulses to the respective ventricles and an AA-delay between consecutive stimulation pulses to the respective atria;
    a sensor adapted for interaction with said subject to measure a parameter associated with cardiac output of said subject and to generate a measurement signal dependent thereon;
    a control unit connected to said pulse generator for controlling emission of stimulation pulses by said pulse generator, said control unit altering at least one of said time delays, as an altered time delay, from a predetermined first value to a second value and back to said first value;
    a windowing unit connected to said sensor and controlled by said control unit to obtain said measurement signal in a first time window during operation of said pulse generator with said at least one altered time delay at said first value, and in a second time window during operation of said pulse generator with said at least one altered time delay at said second value, and in a third time window after returning to operation of said pulse generator with said at least one altered time delay at said first value;
    a calculating unit connected to said windowing unit which calculates respective average values of said measured signal in each of said first, second and third time windows, and generates an output dependent thereon; and
    said control unit being supplied with said output from said calculating unit and determining therefrom, as an optimized value, which of said first and second values of said at least one altered time delay produced a higher cardiac output, and thereafter controlling said pulse generator to operate with said at least one altered time delay at said optimized value.

2. A cardiac pacemaker as claimed in claim 1 wherein said calculating unit generates said output by forming a first difference between the respective average values obtained during said first and second time windows, and a second difference between the respective average values obtained between said second and third time windows.

3. A cardiac pacemaker as claimed in claim 2 wherein said control unit controls said windowing unit to obtain said measured signal in a single continuous time window, as said second time window, during said operation of said pulse generator with said at least one altered time delay at said second value.

4. A cardiac pacemaker as claimed in claim 2 wherein said control unit operates said windowing unit to obtain said measurement signal in a plurality of different time windows, collectively forming said second time window, during said operation of said pulse generator with said at least one altered time delay at said second value, and wherein said calculating unit calculates each of said first difference and said second difference with respect to each of said different time windows.

5. A cardiac pacemaker as claimed in claim 2 wherein said control unit repeatedly alters said at least one altered time delay between said first and second values in a plurality of repetitions, and wherein said calculating unit forms said first difference and said second difference in each of said plurality of repetitions, thereby obtaining a plurality of first differences and a plurality of second differences, and calculates, as said output, an average value of said plurality of first differences and an average value of said plurality of second differences.

6. A cardiac pacemaker as claimed in claim 1 wherein said control unit further controls emission of said stimulation pulses by said pulse generator to alter said at least one of said time delays between said optimized value and a third value and back to said optimized value, and wherein said control unit controls said windowing unit to obtain said measurement signal in a further first time window during operation of said pulse generator with said at least one altered time delay at said optimized value, and in a further second time window during operation of said pulse generator with said at least one altered time delay at said third value, and in a further third time window after returning to operation of said pulse generator with said at least one altered time delay at said optimized value, and wherein said calculating unit calculates a new output from the measurement signals respectively obtained during said further first time window, said further second time window and said further third time window, and wherein said control unit determines a new optimized value from said new output and wherein said control unit repeatedly alters said at least one altered time delay between successive new optimized values and further values until a highest cardiac output is determined.

7. A cardiac pacemaker as claimed in claim 6 wherein said control unit alters said at least one altered time delay a plurality of times between a plurality of values after a predetermined number of operations with said optimized value, and controls said windowing unit to set respective lengths for said windows which are shorter than a time of operation with said optimized value.

8. A cardiac pacemaker as claimed in claim 1 wherein said pulse generator emits said stimulation pulses with time delays further including an AV-delay and wherein said control unit also alters said AV-delay to at least one altered AV-delay, and wherein said control unit determines, dependent on said output from said calculating unit, a combination of said at least one altered time delay and said at least one altered AV-delay which results in a highest cardiac output.

9. A cardiac pacemaker as claimed in claim 1 wherein said control unit operates said pulse generator with said at least one altered time delay at said first value for a time of operation which is equal to a time of operation of said pulse generator with said at least one altered time delay at said second value.

10. A cardiac pacemaker as claimed in claim 1 wherein said control unit operates said pulse generator with said at least one altered time delay at said first value for a time of operation which is different from a time of operation of said pulse generator with said at least one altered time delay at said second value.

11. A cardiac pacemaker as claimed in claim 1 wherein said control unit alters said at least one altered time delay according to a pseudo-stochastic sequence.

12. A cardiac pacemaker as claimed in claim 1 wherein said control unit operates said pulse generator with said at least one altered time delay at said first value for at least one minute and with said at least one altered time delay at said second value for at least one minute.

13. A cardiac pacemaker as claimed in claim 1 wherein said control unit operates said pulse generator with said at least one altered time delay at said first value for a time in a range between 0.5 and 1 minute, and with said at least one altered time delay at said second value for a time in a range between 0.5 and 1 minute.

14. A cardiac pacemaker as claimed in claim 1 wherein said control unit alters said at least one time delay from said first value to said second value at a first alteration time and alters said at least one altered time delay back to said first value at a second alteration time, and controls said windowing unit to position said first time window immediately preceding said first alteration time and to position said second time window immediately following said first alteration time, and to position said third time window immediately following said second alteration time.

15. A cardiac pacemaker as claimed in claim 1 wherein said control unit operates said sensor, via said windowing unit, to sample said parameter at sampling intervals in a range between 2 and 10 seconds.

16. A cardiac pacemaker as claimed in claim 15 wherein said heart has a cardiac cycle detectable by said control unit, and wherein said control unit synchronizes said sampling intervals dependent on said cardiac cycle.

17. A cardiac pacemaker as claimed in claim 1 wherein said sensor is a sensor selected from the group consisting of pO2 sensors, SO2 sensors, average blood pressure sensors, coronary artery flow sensors, and sinus rate sensors.

18. A cardiac pacemaker as claimed in claim 1 wherein said sensor is a blood pressure sensor adapted for measuring blood pressure in the vena cava.

19. A cardiac pacemaker as claimed in claim 1 wherein said sensor is a blood pressure sensor adapted for measuring blood pressure in the right atrium.

* * * * *